(12) United States Patent
Ostrovsky et al.

(10) Patent No.: US 8,968,334 B2
(45) Date of Patent: Mar. 3, 2015

(54) APPARATUS FOR DELIVERING AND ANCHORING IMPLANTABLE MEDICAL DEVICES

(75) Inventors: Isaac Ostrovsky, Wellesley, MA (US); Jozef Slanda, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 470 days.

(21) Appl. No.: 12/760,049

(22) Filed: Apr. 14, 2010

(65) Prior Publication Data

US 2010/0268255 A1    Oct. 21, 2010

Related U.S. Application Data

(60) Provisional application No. 61/170,312, filed on Apr. 17, 2009.

(51) Int. Cl.
| | | |
|---|---|---|
| A61B 17/10 | (2006.01) | |
| A61B 17/06 | (2006.01) | |
| A61B 17/04 | (2006.01) | |
| A61B 17/00 | (2006.01) | |
| A61B 19/00 | (2006.01) | |

(52) U.S. Cl.
CPC ....... *A61B 17/06109* (2013.01); *A61B 17/0401* (2013.01); *A61B 2017/00805* (2013.01); *A61B 2017/0462* (2013.01); *A61B 2017/06042* (2013.01); *A61B 2019/306* (2013.01)
USPC .......................................... 606/139; 606/232

(58) Field of Classification Search
USPC ......... 606/139, 144, 232, 172, 148, 185–189, 606/222–227; 604/117, 178, 179, 180, 181, 604/198
See application file for complete search history.

(56) References Cited

U.S. PATENT DOCUMENTS

| | | | | |
|---|---|---|---|---|
| 527,263 | A * | 10/1894 | Blanchard | 606/223 |
| 4,221,212 | A * | 9/1980 | Miller | 606/187 |
| 4,583,540 | A * | 4/1986 | Malmin | 606/187 |

(Continued)

FOREIGN PATENT DOCUMENTS

| | | |
|---|---|---|
| DE | 202007015955 U1 | 3/2009 |
| EP | 0599772 A1 | 6/1994 |

(Continued)

OTHER PUBLICATIONS http://www.thefreedictionary.com/suture, definition of the term "suture", retrieved May 21, 2012.*

(Continued)

*Primary Examiner* — David Eastwood
(74) *Attorney, Agent, or Firm* — Brake Hughes Bellermann LLP

(57) ABSTRACT

An apparatus includes an elongate member having a distal end portion and a proximal end portion. The elongate member defines a longitudinal axis. The distal end portion of the elongate member defines a notch having a face defining an axis. The axis of the face and the longitudinal axis define an acute angle with respect to a first direction along the longitudinal axis. The notch is configured to retain a loop of a suture when the elongate member is moved through a tissue of a patient in the first direction along the longitudinal axis. The notch is configured to release the loop of the suture when the elongate member is moved through the tissue of the patient in a second direction different than the first direction. The suture has at least one tissue anchor configured to be disposed within the tissue of the patient.

19 Claims, 10 Drawing Sheets

(56) References Cited

U.S. PATENT DOCUMENTS

| | | | |
|---|---|---|---|
| 4,735,615 A * | 4/1988 | Uddo et al. | 604/178 |
| 5,085,661 A * | 2/1992 | Moss | 606/139 |
| 5,149,329 A | 9/1992 | Richardson | |
| 5,217,438 A | 6/1993 | Davis et al. | |
| 5,292,327 A * | 3/1994 | Dodd et al. | 606/148 |
| 5,312,422 A | 5/1994 | Trott | |
| 5,499,991 A * | 3/1996 | Garman et al. | 606/148 |
| 5,520,700 A * | 5/1996 | Beyar et al. | 606/139 |
| 5,571,119 A | 11/1996 | Atala | |
| 5,891,168 A * | 4/1999 | Thal | 606/232 |
| 5,931,855 A | 8/1999 | Buncke | |
| 5,984,933 A * | 11/1999 | Yoon | 606/148 |
| 6,200,330 B1 * | 3/2001 | Benderev et al. | 606/232 |
| 6,306,156 B1 * | 10/2001 | Clark | 606/216 |
| 6,398,787 B1 | 6/2002 | Itoman | |
| 6,423,072 B1 | 7/2002 | Zappala | |
| 6,635,058 B2 * | 10/2003 | Beyar et al. | 606/232 |
| 6,652,561 B1 * | 11/2003 | Tran | 606/232 |
| 6,848,152 B2 | 2/2005 | Genova et al. | |
| 6,932,759 B2 | 8/2005 | Kammerer et al. | |
| 7,377,926 B2 | 5/2008 | Topper et al. | |
| 7,381,212 B2 | 6/2008 | Topper et al. | |
| 7,387,634 B2 | 6/2008 | Benderev | |
| 8,449,573 B2 | 5/2013 | Chu | |
| 8,591,545 B2 * | 11/2013 | Lunn et al. | 606/232 |
| 2001/0037119 A1 * | 11/2001 | Schmieding | 606/139 |
| 2001/0049467 A1 * | 12/2001 | Lehe et al. | 600/30 |
| 2002/0188301 A1 | 12/2002 | Dallara et al. | |
| 2003/0065336 A1 * | 4/2003 | Xiao | 606/144 |
| 2003/0088272 A1 * | 5/2003 | Smith | 606/232 |
| 2003/0120309 A1 * | 6/2003 | Colleran et al. | 606/232 |
| 2003/0171778 A1 | 9/2003 | Lizardi | |
| 2004/0087978 A1 * | 5/2004 | Velez et al. | 606/144 |
| 2004/0098053 A1 | 5/2004 | Tran | |
| 2004/0106847 A1 | 6/2004 | Benderev | |
| 2004/0237736 A1 | 12/2004 | Genova et al. | |
| 2005/0203576 A1 | 9/2005 | Sulamanidze et al. | |
| 2006/0217589 A1 | 9/2006 | Wan et al. | |
| 2006/0282161 A1 | 12/2006 | Huynh et al. | |
| 2007/0016135 A1 * | 1/2007 | Kanner et al. | 604/117 |
| 2007/0038249 A1 | 2/2007 | Kolster | |
| 2007/0129758 A1 * | 6/2007 | Saadat | 606/232 |
| 2008/0103527 A1 | 5/2008 | Martin et al. | |
| 2008/0132931 A1 | 6/2008 | Mueller | |
| 2009/0076529 A1 * | 3/2009 | Ganti | 606/151 |
| 2009/0287245 A1 | 11/2009 | Ostrovsky et al. | |
| 2010/0324357 A1 | 12/2010 | Chu | |
| 2013/0253259 A1 | 9/2013 | Chu | |

FOREIGN PATENT DOCUMENTS

| | | |
|---|---|---|
| FR | 2422386 | 11/1979 |
| FR | 2422386 A | 11/1979 |
| WO | 01/78609 A2 | 10/2001 |
| WO | 2004/112585 A | 12/2004 |
| WO | 2004112585 A2 | 12/2004 |
| WO | 2005122954 A1 | 12/2005 |
| WO | 2006108145 A1 | 10/2006 |
| WO | 2007/098212 A | 8/2007 |
| WO | 2007098212 A2 | 8/2007 |
| WO | 2008087635 A2 | 7/2008 |
| WO | 2009140012 A1 | 11/2009 |

OTHER PUBLICATIONS

International Search Report and Written Opinion for PCT Application No. PCT/US2010/031273, mailed on Dec. 1, 2010, 17 Pages.
Non-Final Office Action for U.S. Appl. No. 12/549,704, mailed Sep. 26, 2011, 13 pages.
Final Office Action for U.S. Appl. No. 12/549,704, mailed Jan. 30, 2012, 30 pages.
Non-Final Office Action for U.S. Appl. No. 12/549,704, mailed Jul. 25, 2012, 10 pages.
Final Office Action Response for U.S. Appl. No. 12/549,704, filed Apr. 27, 2012, 11 pages.
Non-Final Office Action for U.S. Appl. No. 12/394,965, mailed Aug. 8, 2011, 15 pages.
Non-Final Office Action Response for U.S. Appl. No. 12/394,965, filed Nov. 3, 2011, 11 pages.
Non-Final Office Action for U.S. Appl. No. 12/394,965, mailed Mar. 2, 2012, 13 pages.
Restriction Requirement for U.S. Appl. No. 12/394,965, mailed May 18, 2011, 6 pages.
Non-Final Office Action Response for U.S. Appl. No. 12/394,965, filed Jun. 4, 2012, 9 pages.
Restriction Requirement Response for U.S. Appl. No. 12/394,965, filed Jun. 15, 2011, 1 page.
Office Action received for U.S. Appl. No. 12/394,965, mailed on Dec. 7, 2012, 15 pages.
International Search Report and Written Opinion for International Application No. PCT/US2009/040587, mailed on Oct. 21, 2009, 15 pages.
International Preliminary Report on Patentability for PCT Patent Application No. PCT/US2009/040587, mailed on Nov. 25, 2010, 9 pages.
Final Office Action for U.S. Appl. No. 12/394,965, mailed Oct. 31, 2013, 13 pages.
Non-Final Office Action for U.S. Appl. No. 12/394,965, mailed Mar. 21, 2013, 14 pages.
Final Office Action for U.S. Appl. No. 12/394,965, mailed Dec. 7, 2012, 15 pages.

* cited by examiner

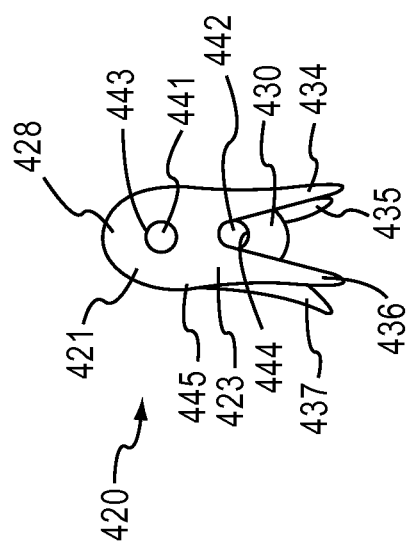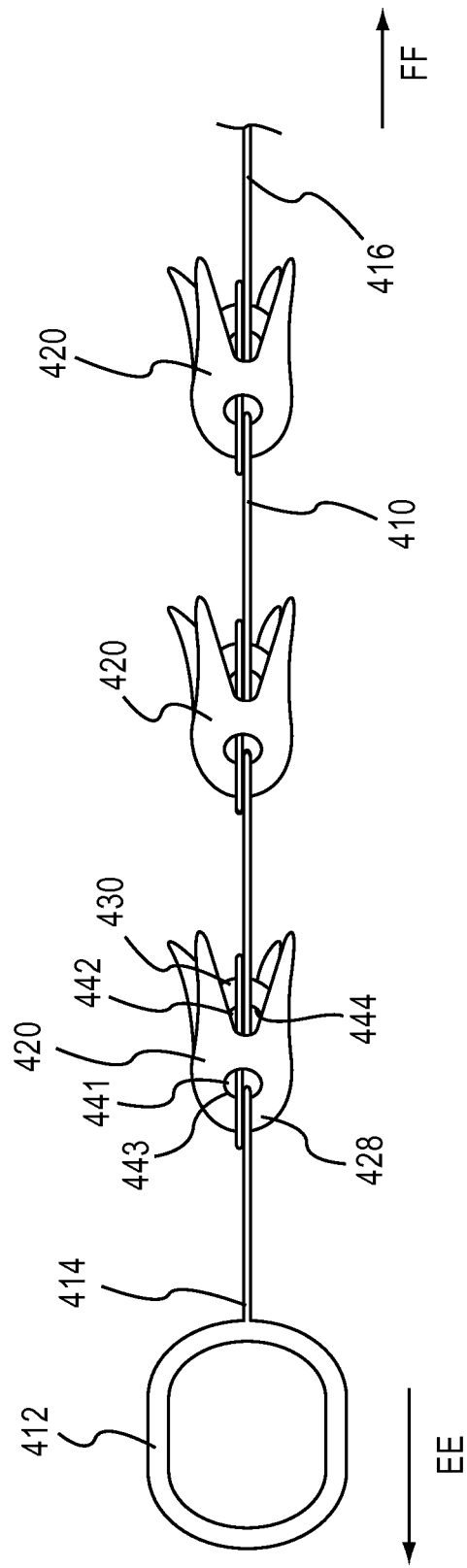

APPARATUS FOR DELIVERING AND ANCHORING IMPLANTABLE MEDICAL DEVICES

CROSS REFERENCE TO RELATED APPLICATIONS

This application is a nonprovisional of, and claims priority to, U.S. Patent Application No. 61/170,312, filed Apr. 17, 2009, entitled "APPARATUS FOR AND METHOD OF DELIVERING AND ANCHORING IMPLANTABLE MEDICAL DEVICES", which is incorporated by reference herein in its entirety.

BACKGROUND

This invention relates to a medical device and more particularly to methods and devices for delivering a suture including tissue anchors.

Sutures including tissue anchors have application to a wide variety of surgical procedures including those that require high anchoring strength. For example, one such procedure is directed to female urinary incontinence and involves insertion of a suture to be fixed to bodily tissue under and/or lateral to the urethra to reconstitute the ligamentary support for the urethra. Generally, the suture is inserted into two or more body tissues to couple the body tissues tightly together without knotting the suture.

In other procedures a suture having tissue anchors is coupled to an implant that is configured to support a portion of a body of a patient. In such a procedure, the tissue anchor must be able to support the implant without tearing through the tissue within which it is disposed.

Tissue anchors that are large or have many barbs are often difficult to insert into a tissue. When inserting such tissue anchors, a large incision is often necessary and bulky delivery tools are often used. Using a large incision or bulky delivery tools causes unwanted trauma to the tissue and can weaken the tissue within which the tissue anchor is disposed. Thus, a need exists for devices and methods that can be used to effectively deliver a suture having tissue anchors to a tissue of a patient.

SUMMARY

An apparatus includes an elongate member having a distal end portion and a proximal end portion. The elongate member defines a longitudinal axis. The distal end portion of the elongate member defines a notch having a face defining an axis. The axis of the face and the longitudinal axis define an acute angle with respect to a first direction along the longitudinal axis. The notch is configured to retain a loop of a suture when the elongate member is moved through a tissue of a patient in the first direction along the longitudinal axis. The notch is configured to release the loop of the suture when the elongate member is moved through the tissue of the patient in a second direction different than the first direction. The suture has at least one tissue anchor configured to be disposed within the tissue of the patient.

BRIEF DESCRIPTION OF THE DRAWINGS

FIG. 6 is a side view of multiple tissue anchors coupled to a suture, according to an embodiment.

FIG. 7 is a side view of a tissue anchor shown in FIG. 6.

DETAILED DESCRIPTION

Figure 1:
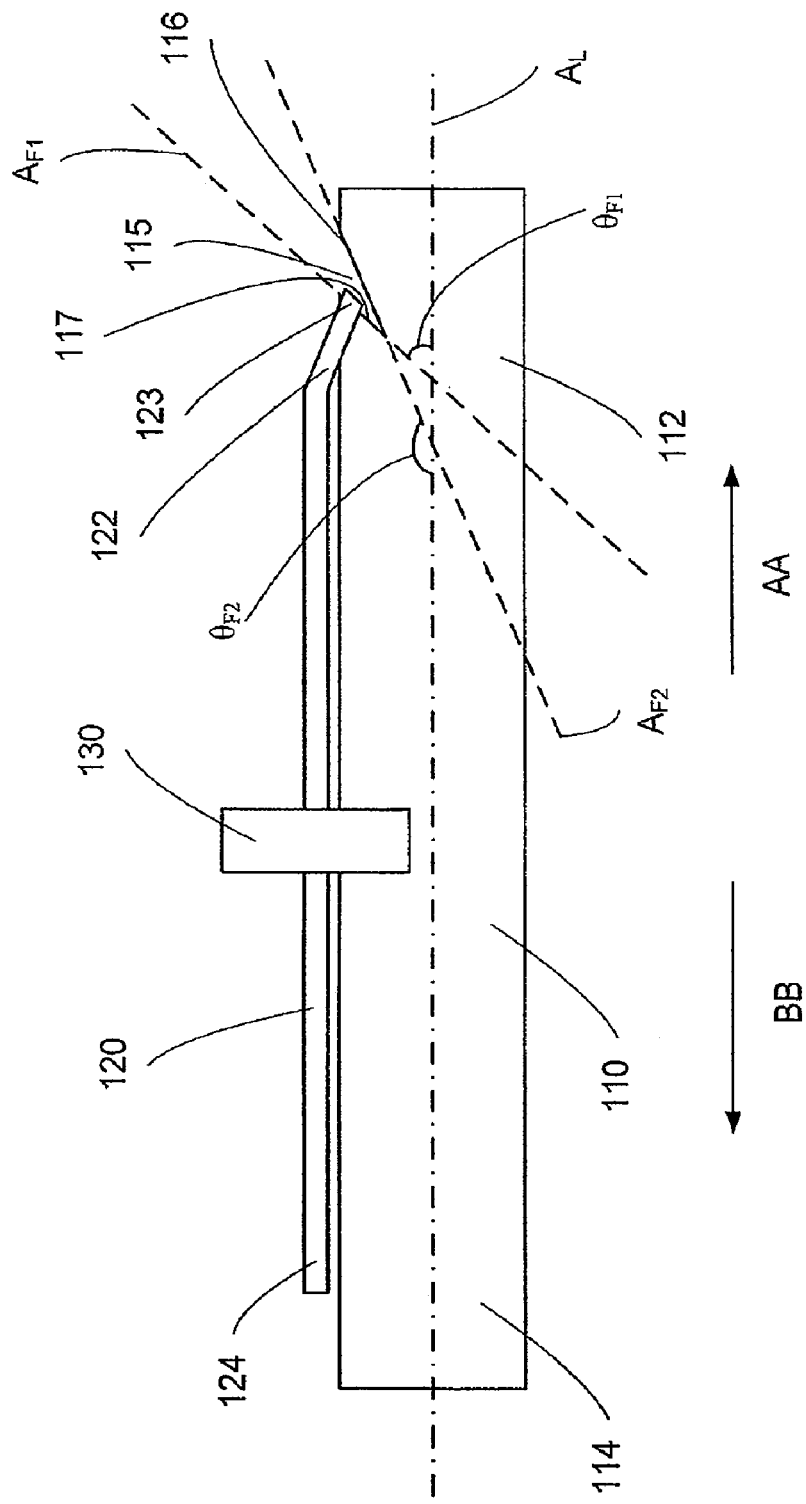
FIG. 1 is a schematic illustration of a suture attached to a delivery device, according to an embodiment.

In some embodiments, an apparatus includes an elongate member having a distal end portion and a proximal end portion. The elongate member defines a longitudinal axis. The distal end portion of the elongate member defines a notch having a face defining an axis. The axis of the face and the longitudinal axis define an acute angle with respect to a first direction along the longitudinal axis. The notch is configured to retain a loop of a suture when the elongate member is moved through a tissue of a patient in the first direction along the longitudinal axis. The notch is configured to release the loop of the suture when the elongate member is moved through the tissue of the patient in a second direction different than the first direction. The suture has at least one tissue anchor configured to be disposed within the tissue of the patient.

In some embodiments, an apparatus includes an elongate member and an adjustable stop. The elongate member has a distal end portion and a proximal end portion. The distal end portion of the elongate member defines a notch configured to releasably retain a loop of a suture when the elongate member is inserted into a tissue of a patient a distance. The adjustable stop is movably coupled to the elongate member. The adjustable stop is configured to allow a user to determine the distance the elongate member is inserted into the tissue.

In some embodiments, an apparatus includes an elongate member having a distal end portion and a proximal end portion. The elongate member defines a longitudinal axis and an outer perimeter. The distal end portion of the elongate member has a tissue piercing tip and an oblique shoulder facing toward the tissue piercing tip. The oblique shoulder is disposed proximal to the tissue piercing tip along the longitudinal axis and is within the outer perimeter defined by the elongate member.

In some embodiments, a medical device includes an elongate member, a suture and an anchor. The elongate member has a distal end portion and a proximal end portion. The distal end portion of the elongate member defines a notch. The suture has a distal end portion and a proximal end portion. The distal end portion of the suture has a loop configured to be inserted into the notch. The notch is configured to retain the loop of the suture when the elongate member is inserted into a tissue of a patient. The anchor is coupled to the suture and configured to retain the suture within the tissue of the patient when the suture is disposed within the tissue of the patient and the elongate member is removed from the tissue of the patient.

In some embodiments, a method of inserting a suture within a body of a patient includes sliding an adjustable stop along an elongate member. A loop of a suture is attached to a distal end portion of the elongate member. A tissue anchor is coupled to the suture. The tissue anchor is inserted into a tissue of a patient by moving the elongate member through the tissue of the patient until the adjustable stop contacts an outer surface of the tissue of the patient. The distal end portion of the elongate member is disposed within the tissue a distance from the outer surface of the tissue. The distance from the outer surface of the tissue is substantially equal to a distance between the distal end portion of the elongate member and the adjustable stop. The loop of the suture is the released from the distal end portion of the elongate member and the elongate member is removed from the body of the patient.

As used herein, the terms proximal portion or proximal end refer to the portion or end, respectively, of a device that is closest to a medical practitioner (e.g., a physician) when performing a medical procedure, and the terms distal portion or distal end refer to the portion or end, respectively, of the device that is furthest from the physician during a medical procedure. For example, the end of a medical device first inserted inside the patient's body would be the distal end of the medical device, while the end of the medical device handled by the medical practitioner would be the proximal end of the medical device.

FIG. 1 is a schematic illustration of a suture 120 attached to a delivery device 110, according to an embodiment. The suture 120 includes a proximal end portion 124, a distal end portion 122 and a tissue anchor 130. The suture 120 can be made of any biocompatible material. For example, the suture 120 can be a monofilament suture, a braided suture, a tape, a mesh, include a mesh-like material and/or any other material known in the art. In some embodiments, the suture is similar to the sutures shown and described in U.S. Provisional Patent Application No. 61/071,726 entitled "Surgical Composite Barbed Suture," filed on May 14, 2008, which is hereby incorporated by reference in its entirety.

The proximal end portion 124 of the suture 120 is configured to be attached to any device configured to be retained within a body of a patient, such as an implant (not shown in FIG. 1). Such an implant can be configured to be placed within a body of a patient and can be configured to support a portion of the body. For example, the implant can be similar to the implants or grafts disclosed in U.S. Patent Application No. 61/017,257 entitled "Apparatus and Method for Uterine Preservation," filed on Dec. 28, 2007, which is hereby incorporated by reference in its entirety. The implant can be a variety of different shapes, sizes and configurations depending on the intended use for the particular implant. In some embodiments, the implant can be substantially rectangular, square, oval, or elliptical. The implant can be shaped and sized to support a bladder and/or a bladder neck (e.g., to treat a cystocele), a uterus (e.g., to treat a hysterocele) and/or a rectum (e.g. to treat a rectocele).

The implant can be formed with a mesh material to allow tissue in-growth to the implant after implantation. For example, some or all of the implant can be formed with a mesh material as described in U.S. Patent Pub. 2005/0038452 A1 to Chu, the disclosure of which is hereby incorporated by reference in its entirety. In some embodiments, some or all of the implant can be formed with the Advantage® Mesh or the Polyform™ Synthetic Mesh material each provided by Boston Scientific Corporation.

The distal end portion 122 of the suture 120 includes an attachment portion 123 configured to be releasably attached to the delivery device 110, described in further detail herein. In some embodiments, the attachment portion 123 of the distal end portion 122 of the suture 120 can be, for example, a loop configured to be inserted into a notch 115 of the delivery device 110. In other embodiments, the attachment portion can be a clip, an adhesive portion, and/or any other attachment mechanism known in the art.

The tissue anchor 130 can be any device configured to retain the suture 120 within a tissue of a patient. In some embodiments, for example, the tissue anchor 130 is similar to the tissue anchors shown and described in U.S. Provisional Patent Application No. 61/071,726 entitled "Surgical Composite Barbed Suture," filed on May 14, 2008, which is hereby incorporated by reference in its entirety.

The tissue anchor 130 is configured to retain its position with respect to bodily tissue when inserted into bodily tissue. In some embodiments, the tissue anchor 130 includes a retaining member, for example, a barb, a prong, a tab, and/or any other retaining member known in the art. In other embodiments, the tissue anchor includes multiple retaining members extending from the elongate member. In some embodiments, the retaining members can flex or bend to facilitate insertion into bodily tissue. In other embodiments, the retaining members are rigid and are not configured to bend or flex during insertion.

The tissue anchor 130 is constructed of any suitable material. In some embodiments, for example, the tissue anchor 130 is constructed of a biocompatible polymer, a metal, and/or any other material known in the art. In some embodiments, the tissue anchor 130 includes an opaque material to increase the visibility of the medical practitioner during insertion of the suture 120.

The tissue anchor 130 is coupled to the suture 120 by any suitable means. In some embodiments, for example, the tissue anchor 130 is coupled to the suture 120 via a knot, an adhesive, such as, for example, glue, and/or any other attachment mechanism known in the art. In other embodiments, the tissue anchor is monolithically formed with the suture and/or molded to the suture. In some embodiments, the tissue anchor 130 is coupled near the distal end portion 122 of the suture 120. In such embodiments, the distal end portion 112 of the delivery device 110 need not be inserted as far into the body of the patient for the tissue anchor 130 to be disposed within the tissue of the patient. This decreases the trauma caused to the tissue of the patient beyond the portion of the tissue where the tissue anchor 130 is disposed.

The delivery device 110 includes a distal end portion 112 and a proximal end portion 114 and defines a longitudinal axis $A_L$. The delivery device 110 is configured to be moved through a tissue of a patient in a direction substantially parallel to the longitudinal axis $A_L$. In some embodiments, the delivery device 110 is substantially rigid and/or solid. In other embodiments, the delivery device defines a lumen. The proximal end portion 114 of the delivery device 110 is controlled by the medical practitioner directly by holding the proximal end portion 114 or indirectly by controlling another device coupled to the proximal end portion 114 when the distal end portion 112 of the delivery device 110 is inserted into the tissue of the patient.

The distal end portion 112 of the delivery device 110 defines a notch 115 or a shoulder configured to releasably retain the attachment portion 123 of the distal end portion 122 of the suture 120. The notch 115 includes a first face 117 and a second face 116. The first face 117 defines an axis $A_{F1}$. In other embodiments, the notch only includes a first face. In some embodiments, the notch 115 or shoulder is within an outer parameter defined by the delivery device 110. In other embodiments, the notch or shoulder extends outside the outer parameter defined by the delivery device.

The axis $A_{F1}$ of the first face 117 defines an angle $S_{F1}$ with the longitudinal axis AL. The angle $S_{F1}$ defined by the axis $A_{F1}$ of the first face 117 and the longitudinal axis AL is acute with respect to a first direction shown by the arrow AA in FIGS. 1 and 2. The angle $S_{F1}$ is configured to retain the attachment portion 123 of the suture 120 when the delivery device 110 is moved in the first direction AA, as described in further detail herein.

Similarly, the second face 116 defines an axis $A_{F2}$. The axis $A_{F2}$ of the second face 116 defines an angle $0_{F2}$ with the longitudinal axis AL. The angle $0_{F2}$ defined by the axis $A_{F2}$ of the second face 116 and the longitudinal axis $A_L$ is obtuse with respect to a second direction shown by the arrow BB in FIGS. 1 and 3. The angle $0_{F2}$ is configured to allow the attachment portion 123 of the suture 120 to become uncoupled from the notch 115 of the delivery device 110 when the delivery device 110 is moved in the second direction BB, as described in further detail herein.

The distal end portion 112 of the delivery device 110 is configured to be inserted into the body of the patient to assist in delivering the suture 120 within a tissue of the patient. In some embodiments, the distal end portion includes a tapered portion configured to pierce and/or dilate tissue as the delivery device is inserted into the tissue of the patient.

In use, the suture 120 is attached to the delivery device 110 by attaching the attachment portion 123 of the distal end portion 122 of the suture 120 to the notch 115 defined by the delivery device 110. In some embodiments, this includes inserting a loop of the suture 120 into the notch 115 of the delivery device 110. The proximal end portion 124 of the suture 120 is aligned substantially parallel to the longitudinal axis AL defined by the delivery device 110. Said another way, a longitudinal axis defined by the suture is aligned such that it is substantially parallel to the longitudinal axis AL defined by the delivery device 110. Positioning the suture 120 along the longitudinal axis AL allows the suture 120 to be inserted into the tissue of the patient through a lumen created by the delivery device 110 as the delivery device 110 moves through the tissue of the patient.

Figure 2:
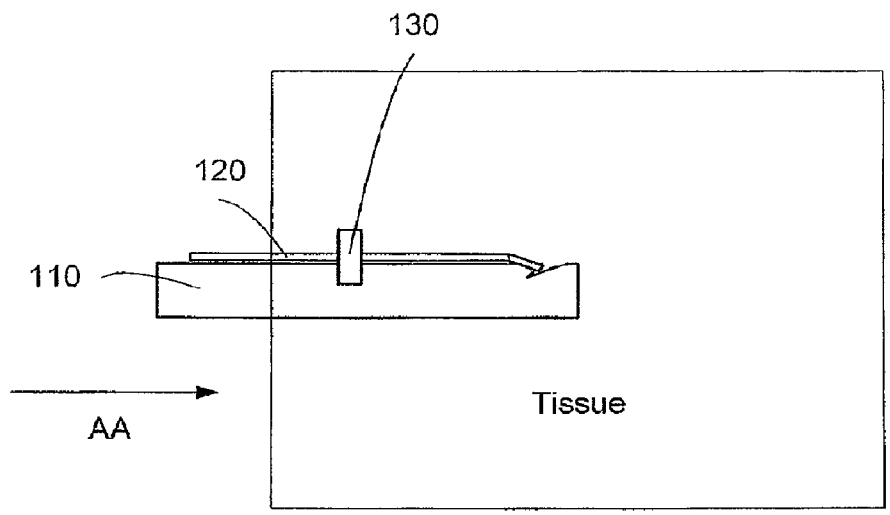
FIGS. 2 and 3 are schematic illustrations of the delivery device of FIG. 1 inserting the suture of FIG. 1 into a tissue of a patient.
Figure 3:
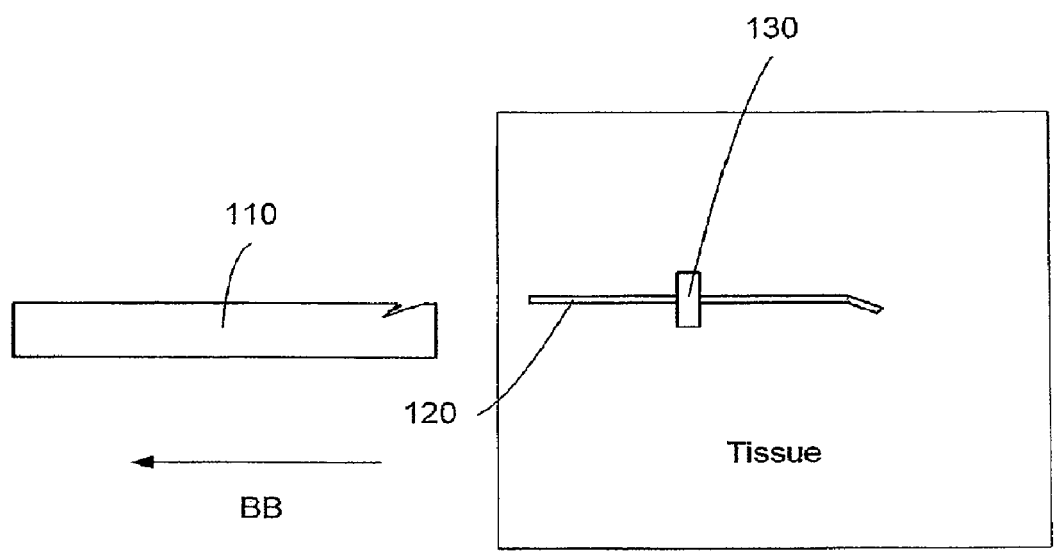

FIGS. 2 and 3 are schematic illustrations of the delivery device 110 inserting the suture 120 into a tissue of a patient. The delivery device 110 and the suture 120 are inserted into the tissue of the patient by moving the delivery device 110 with respect to the tissue in a first direction along the longitudinal axis AL shown by the arrow AA in FIG. 2. The first face 117 of the notch 115 exerts a force on the attachment portion 123 of the suture 120 that is normal to the first face 117 of the notch 115 as the delivery device 110 is moved in the first direction AA. Because the angle $S_{F1}$ defined by the axis $A_{F1}$ of the first face 117 of the notch 115 is acute with respect to the first direction AA, the force exerted on the attachment portion 123 of the suture 120 by the first face 117 of the notch 115 retains the attachment portion 123 of the suture 120 in the notch 115 as the delivery device 110 is moved in the first direction AA.

Once the tissue anchor 130 reaches a depth within the tissue where it is to be disposed, the medical practitioner can release the attachment portion 123 of the suture 120 from the notch 115 of the delivery device 110 by moving the delivery device 110 in a second direction along the longitudinal axis AL shown by the arrow BB in FIG. 3. The second direction BB is substantially opposite the first direction AA. Because the angle $S_{F2}$ defined by the axis $A_{F2}$ of the second face 116 of the notch 115 and the longitudinal axis AL is obtuse with respect to the second direction BB, the attachment portion 123 of the suture 120 is released from the notch 115 as the delivery device 110 is moved in the second direction BB.

Said another way, when the delivery device 110 is moved in the second direction BB, the second face 116 of the notch 115 exerts a force on the attachment portion 123 of the suture 120 that is normal to the second face 116. This force pushes the attachment portion 123 of the suture 120 out of the notch 115. Once the attachment portion 123 of the suture 120 is released from the notch 115, the medical practitioner can remove the delivery device 110 from the tissue of the patient by continuing to move the delivery device 110 in the second direction BB.

Figure 4:
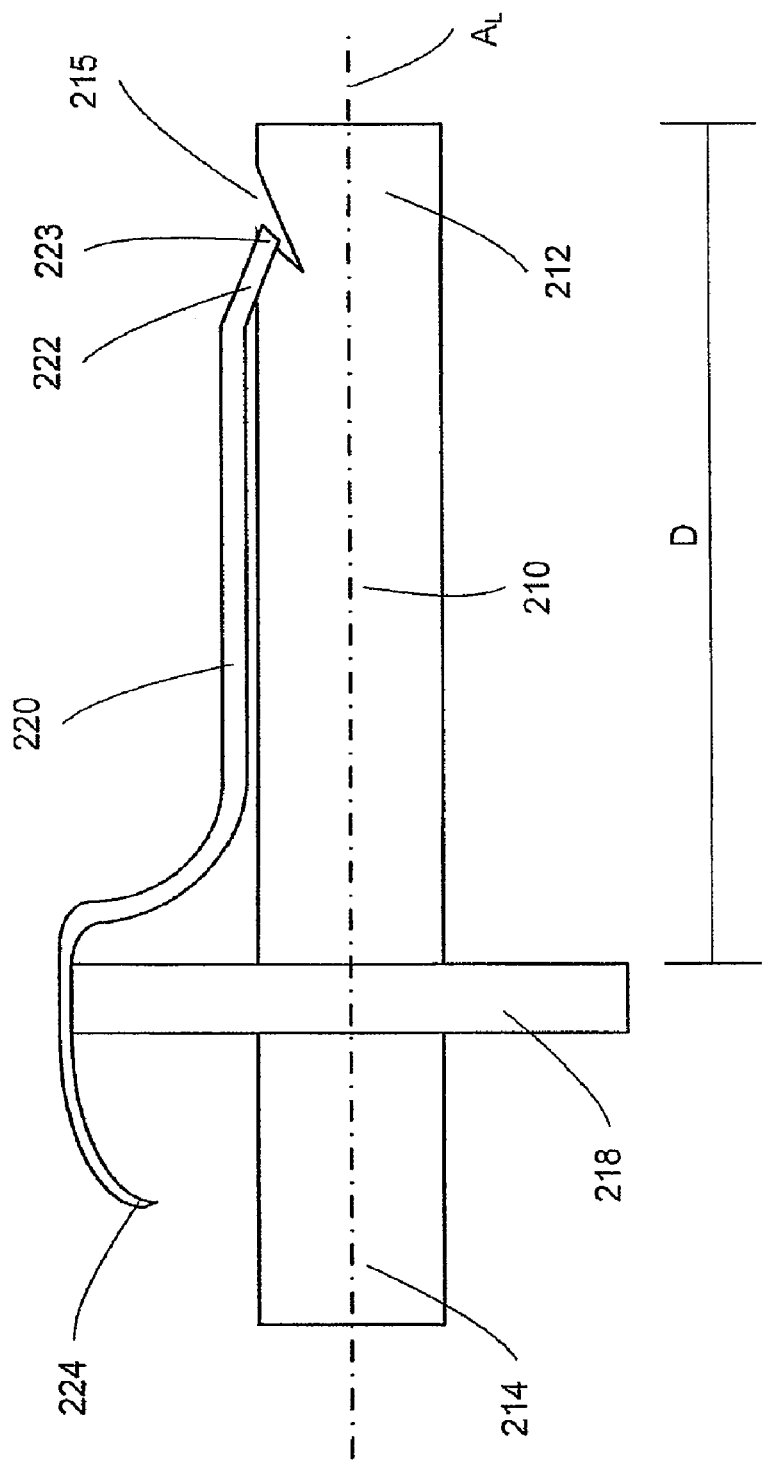
FIG. 4 is a schematic illustration of a suture attached to a delivery device, according to an embodiment.

FIG. 4 is a schematic illustration of a suture 220 attached to a delivery device 210, according to another embodiment. The suture 220 includes a proximal end portion 224, and a distal end portion 222. The proximal end portion 224 of the suture 220 is configured to be attached to any device configured to be retained within a body of a patient, such as an implant (not shown in FIG. 4).

The distal end portion 222 of the suture 220 includes an attachment portion 223 configured to be releasably attached to the delivery device 210. In some embodiments, the attachment portion 223 of the distal end portion 222 of the suture 220 can be, for example, a loop configured to be inserted into a notch 215 of the delivery device 210. In other embodiments, the attachment portion 223 can be a clip, an adhesive portion, and/or any other attachment mechanism known in the art.

In some embodiments, the suture 220 includes a tissue anchor (not shown in FIG. 4) and/or another device configured to assist in retaining the suture within the tissue of the patient. In other embodiments, the suture does not include a tissue anchor. In such embodiments, the friction between the tissue surrounding the suture and the suture can help retain the suture within the tissue.

The delivery device 210 includes a distal end portion 212 and a proximal end portion 214 and defines a longitudinal axis AL. The delivery device 210 is configured to be moved through a tissue of a patient in a direction substantially parallel to the longitudinal axis AL. In some embodiments, the delivery device 210 is substantially rigid and/or solid. In other embodiments, the delivery device defines a lumen. The proximal end portion 214 of the delivery device 210 is controlled by the medical practitioner directly by holding the proximal end portion 214 or indirectly by controlling another device coupled to the proximal end portion 214 when the distal end portion 212 of the delivery device 210 is inserted into the tissue of the patient.

The distal end portion 212 of the delivery device 210 defines a notch 215 or a shoulder configured to releasably retain the attachment portion 223 of the distal end portion 222 of the suture 220. The distal end portion 212 of the delivery device 210 is configured to be inserted into the body of the patient to assist in delivering the suture 220 within a tissue of the patient. In some embodiments, the distal end portion includes a tapered portion configured to pierce and/or dilate tissue as the delivery device is inserted into the tissue of the patient.

An adjustable stop 218 is movably coupled to the delivery device 210. The adjustable stop 218 is configured to be disposed in at least two positions with respect to the delivery device 210. In some embodiments, for example, the adjustable stop 218 has a first configuration and a second configuration. When the adjustable stop 218 is in its first configuration, the location of the adjustable stop 218 with respect to the delivery device 210 is fixed. Said another way, when the adjustable stop 218 is in its first configuration it cannot slide with respect to the delivery device 210. Accordingly, when the adjustable stop 218 is in its first configuration, the distance D shown in FIG. 4 does not change and the adjustable stop's 218 position with respect to the delivery device 210 is fixed. When the adjustable stop 218 is in its second configuration it is configured to slide with respect to the delivery device 210 in a direction substantially along the longitudinal axis AL.

In other embodiments, the adjustable stop does not slide with respect to the delivery device but instead is coupled to the delivery device in a desired location with respect to the delivery device. In such embodiments, in order to move the adjustable stop with respect to the delivery device the adjustable stop is uncoupled from the delivery device and recoupled to the delivery device in another location.

The adjustable stop 218 is configured to help limit the distance that the distal end portion 212 of the delivery device 210 can be inserted into the tissue of the patient. The distance that the distal end portion 212 of the delivery device 210 can be inserted into the patient is substantially equal to the distance between the distal end portion 212 of the delivery device 210 and the adjustable stop 218 shown as distance D in FIG. 4. Having an adjustable stop 218 prevents a medical practitioner from inserting the distal end portion 212 of the delivery device 210 into the tissue of the patient further than expected, causing unwanted harm to the patient. The adjustable stop 218 also provides the medical practitioner with the ability to determine a depth within the tissue of the patient where the distal end portion 224 of the suture 220 is to be disposed, and, using the adjustable stop 218, set the delivery device 210 to deliver the distal end portion 224 of the suture 220 to this depth, as further described in detail herein.

In use, the medical practitioner moves the adjustable stop 218, in its second configuration, with respect to the delivery device 210 to adjust the distance D between the distal end portion 212 of the delivery device 210 and the adjustable stop 218. As discussed above, the distance D corresponds to the depth the distal end portion 212 of the delivery device can be inserted into the tissue of the patient. Once the adjustable stop 218 is in the position along the delivery device 210 that corresponds to the desired depth, the adjustable stop 218 is moved from its second configuration to its first configuration. As discussed above, when the adjustable stop 218 is in its first configuration, the location of the adjustable stop 218 with respect to the delivery device 210 is fixed. Accordingly, the desired depth cannot be inadvertently changed prior to and/or during the insertion process.

The suture 220 is attached to the delivery device 210 by attaching the attachment portion 223 of the distal end portion 222 of the suture 220 to the notch 215 defined by the delivery device 210. In some embodiments, this includes inserting a loop of the suture 220 into the notch 215 of the delivery device 210. The proximal end portion 224 of the suture 220 is aligned substantially parallel to the longitudinal axis AL defined by the delivery device 210. Once the adjustable stop 218 has been adjusted and moved to its first configuration and the suture 220 has been attached to the delivery device 210, the suture 220 can be inserted into the tissue of the patient similar to suture 120.

Figure 5:
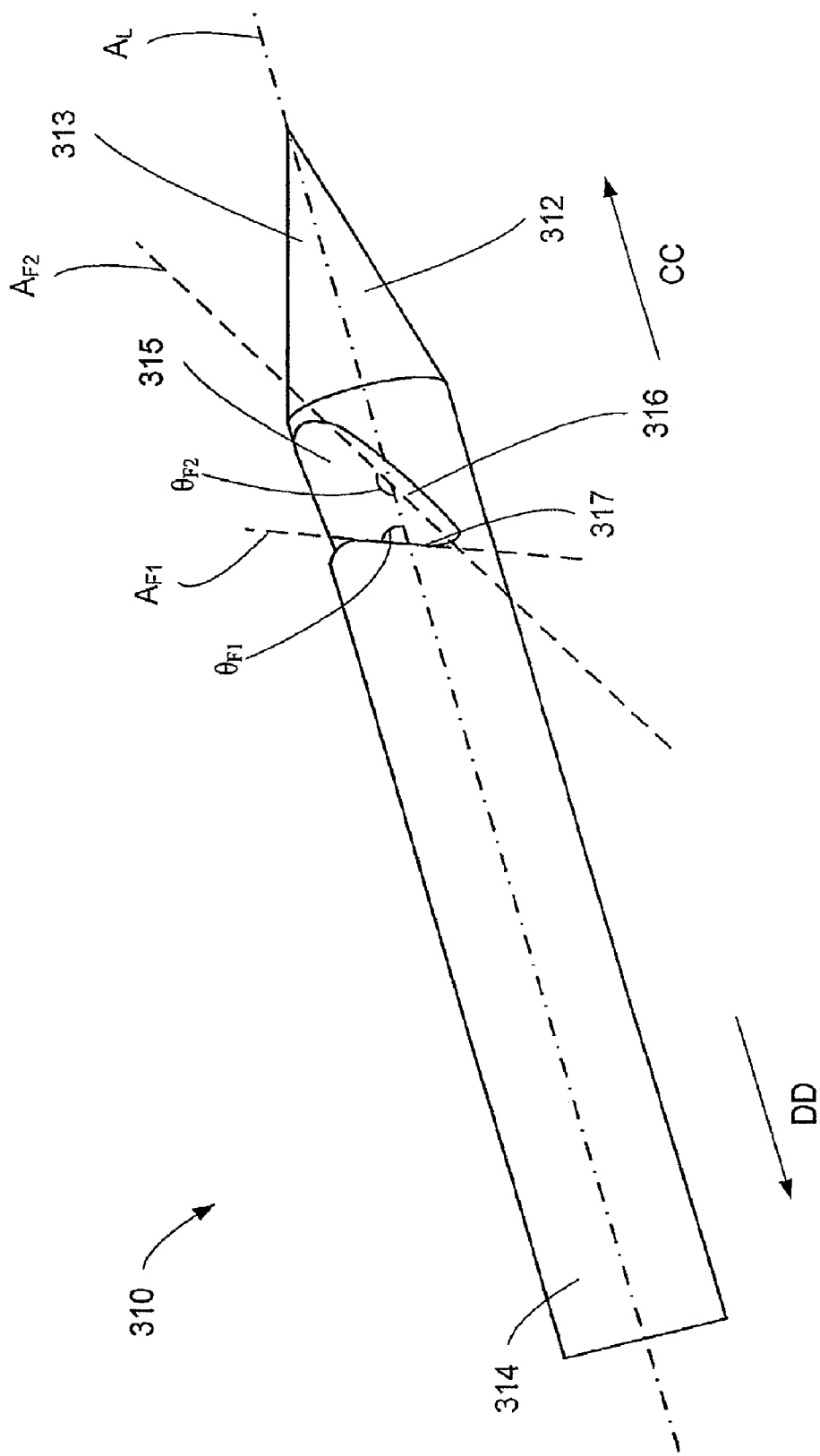
FIG. 5 is a perspective view of a delivery device, according to an embodiment.

FIG. 5 is a perspective view of a delivery device 310 configured to deliver a suture within a tissue of a patient, according to another embodiment. The delivery device 310 includes a distal end portion 312 and a proximal end portion 314 and defines a longitudinal axis $A_L$. The delivery device 310 is configured to be moved through the tissue of the patient in a direction substantially parallel to the longitudinal axis AL. In some embodiments, the delivery device 310 is substantially rigid and/or solid. In other embodiments, the delivery device defines a lumen. The proximal end portion 314 of the delivery device 310 is controlled by the medical practitioner directly by holding the proximal end portion 314 or indirectly by controlling another device coupled to the proximal end portion 314 when the distal end portion 312 of the delivery device 310 is inserted into the tissue of the patient.

The proximal end portion 314 of the delivery device 310 is configured to be held by a medical practitioner and/or indirectly controlled by a medical practitioner when the distal end portion 312 of the delivery device is inserted into the tissue of the patient.

The distal end portion 312 of the delivery device 310 includes a tapered portion 313 and defines a notch 315 or a shoulder. The distal end portion 312 of the delivery device 310 is configured to be inserted into the tissue of the patient to assist in delivering a suture within the tissue of the patient. The tapered portion 313 of the distal end portion 312 has a sharp tip configured to pierce the tissue and is tapered. This allows the tapered portion 313 to dilate tissue as the delivery device 310 is inserted into the tissue of the patient. Accordingly, the tapered portion 313 pierces and dilates a tissue in which a suture will be disposed.

The notch 315 defined by the distal end portion 312 of the delivery device 310 is configured to releasably retain an attachment portion of a suture. The attachment portion of the suture can be, for example, a loop on the distal end portion of the suture and/or any other attachment mechanism known in the art. The notch 315 includes a first face 317 and a second face 316. In other embodiments, the notch includes only a first face. In some embodiments, the notch 315 or shoulder is within an outer parameter defined by the delivery device 310. In other embodiments, the notch or shoulder extends outside the outer parameter defined by the delivery device.

The first face 317 defines an axis $A_{F1}$. The axis $A_{F1}$ of the first face 317 defines an angle 8F1 with the longitudinal axis AL. The angle 8F1 defined by the axis $A_{F1}$ of the first face 317 and the longitudinal axis AL is acute with respect to a first direction shown by the arrow CC in FIG. 5. The angle 8F1 is configured to retain the attachment portion of the suture 320 when the delivery device 310 is moved in the first direction CC, as described in further detail herein.

Similarly, the second face 316 defines an axis $A_{F2}$. The axis $A_{F2}$ of the second face 316 defines an angle $O_F$ with the longitudinal axis $A_L$. The angle $O_{F2}$ defined by the axis $A_{F2}$ of the second face 316 and the longitudinal axis AL is obtuse with respect to a second direction shown by the arrow DD in FIG. 5. The angle $O_{F2}$ is configured to allow the attachment portion of the suture to become uncoupled from the notch 315 of the delivery device 310 when the delivery device 310 is moved in the second direction DD, as described in further detail herein.

FIGS. 6 and 7 show a side view of multiple tissue anchors 420 coupled to a suture 410 and a perspective view of a tissue anchor 420, respectively, according to another embodiment. The suture 410 includes a distal end portion 414 and a proximal end portion 416. The suture 410 can be made of any biocompatible material. For example, the suture 410 can be a monofilament suture, a braided suture, a tape, a mesh, include a mesh-like material and/or any other material known in the art.

The distal end portion 414 of the suture 410 includes a loop 412. The loop 410 is configured to be releasably coupled to a delivery device, as described in further detail herein. In some embodiments, for example, the loop 412 is configured to be releasably coupled to a notch of a delivery device such as the notch 315 of delivery device 310. In other embodiments, the suture can include other attachment mechanisms, such as, for example, a clip, an adhesive portion, and/or any other attachment mechanism known in the art.

The tissue anchor 420 has a first end portion 421 and a second end portion 423 opposite the first end portion 421. As shown in FIG. 6, the first end portion 421 of the tissue anchor 420 includes a coupling portion 428 coupled to the suture 410. The second end portion 423 of the tissue anchor 420 includes a coupling portion 430 coupled to the suture 410. Specifically, the tissue anchor 420 has a first side portion 445 and a second side portion (not shown) opposite the first side portion 445. The tissue anchor 420 defines a first opening 441 that extends from the first side portion 445 to the second side portion. The coupling portion 428 of the first end portion 421 includes the inner wall 443 of the first opening 441 such that when the suture 410 is coupled to the first end portion 421, the suture 410 engages the inner wall 443 of the first opening 441 of the first end portion 421 as shown in FIG. 6. Similarly, the tissue anchor 420 defines a second opening 442 that extends from the first side portion 445 to the second side portion. The coupling portion 430 of the second end portion 423 includes an inner wall 444 of the second opening 442 of the second end portion 423 such that when the suture 410 is coupled to the second end portion 423 the suture 410 engages the inner wall 444 of the second opening 442 of the second end portion 423 as shown in FIG. 6.

As shown in FIG. 6, the suture 410 is coupled to the first end portion 421 and the second end portion 423. Specifically, a portion of the inner wall 443 of the first opening 441 is disposed within a first knot formed by the suture 410. Similarly, a portion of the inner wall 444 of the second opening 442 is disposed within a second knot formed by the suture 410. In some embodiments, the suture 410 can form more or less than two knots. In other embodiments, the tissue anchor can be coupled to the suture in any suitable manner. For example, the tissue anchor can be coupled to the suture via the methods shown and described in U.S. Provisional Patent Application No. 61/071,726 entitled "Surgical Composite Barbed Suture," filed on May 14, 2008, which is hereby incorporated by reference in its entirety.

The tissue anchor 420 includes multiple retaining members 434, 435, 436, 437. The retaining members 434, 435, 436, 437 are configured to allow movement of the suture 410 with respect to the tissue through the tissue of the patient in a first direction shown by the arrow EE in FIG. 6. This allows the suture 410 to pass through the tissue of the patient when being inserted into the tissue of the patient, as further described herein. The retaining members 434, 435, 436, 437 help limit the movement of the suture 410 with respect to the tissue in a second direction, substantially opposite the first direction shown by the arrow FF in FIG. 6. Accordingly, once the suture 410 is placed within the tissue of the patient the anchors 420 help prevent the suture 410 from inadvertently becoming dislodged from the tissue.

Figure 8:
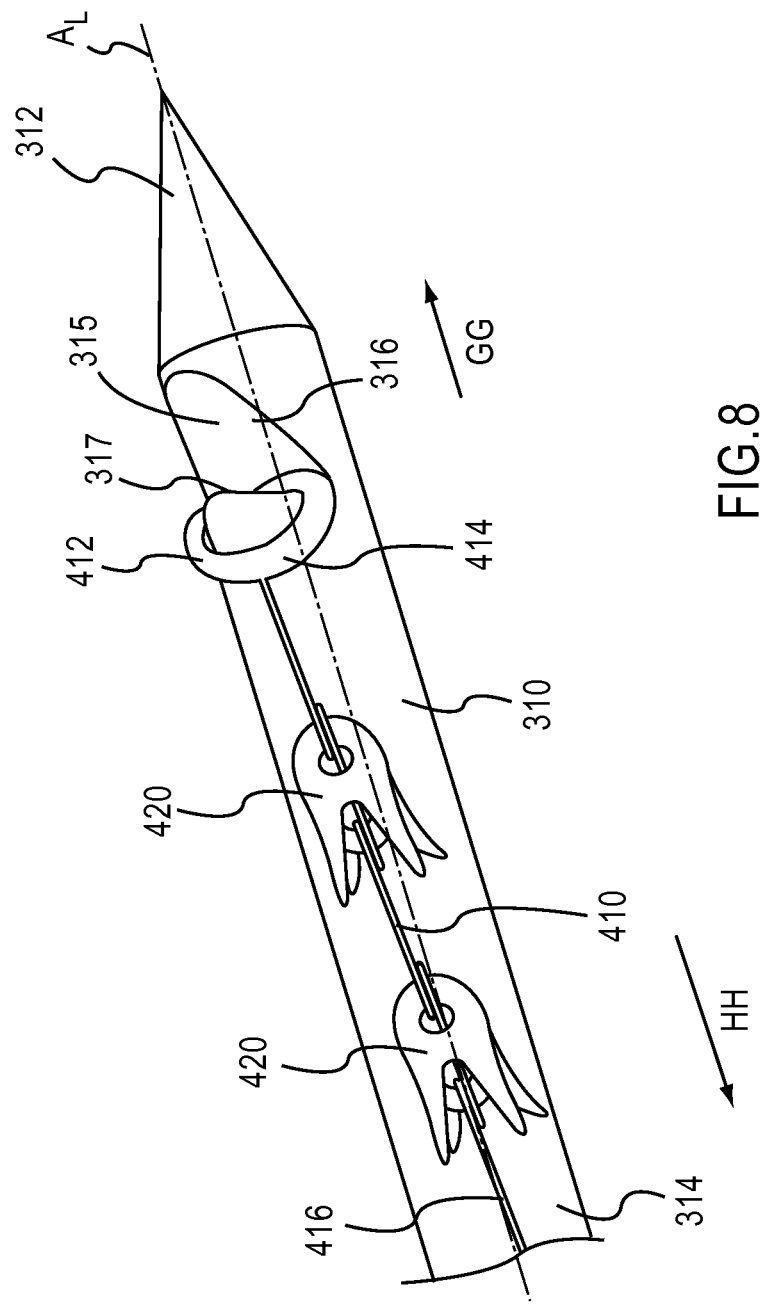
FIG. 8 is a perspective view of the suture of FIG. 6 attached to the delivery device of FIG. 5.

FIG. 8 is a side perspective view of the suture 410 shown in FIG. 6 attached to the delivery device 310 shown in FIG. 5. The suture 410 is attached to the delivery device 310 by attaching the loop 412 of the suture 410 to the notch 315 defined by the delivery device 310. The proximal end portion 416 of the suture 410 is aligned substantially parallel to the longitudinal axis AL defined by the delivery device 310. Said another way, a longitudinal axis defined by the suture is aligned such that it is substantially parallel to the longitudinal axis AL defined by the delivery device 310. Positioning the suture 410 along the longitudinal axis AL allows the suture 410 to be inserted into the tissue of the patient through a lumen created by the delivery device 310 as the delivery device 310 moves through the tissue of the patient.

The delivery device 310 and the suture 410 are inserted into the tissue of the patient by moving the delivery device 310 with respect to the tissue in a first direction along the longitudinal axis AL shown by the arrow GG in FIG. 8. The first face 317 of the notch 315 exerts a force on the loop 412 of the suture 410 that is normal to the first face 317 of the notch 315 as the delivery device 310 is moved in the first direction GG. Because the angle $0_{F1}$ defined by the axis $A_{F1}$ of the first face 317 of the notch 315 and the longitudinal axis $A_L$ is acute with respect to the first direction GG, the force exerted on the loop 412 of the suture 410 by the first face 317 of the notch 315 retains the loop 412 of the suture 410 in the notch 315 as the delivery device 310 is moved in the first direction GG.

Once the tissue anchor 420 reaches a depth within the tissue where it is to be disposed, the medical practitioner can release the loop 412 of the suture 410 from the notch 315 of the delivery device 310 by moving the delivery device 310 in a second direction along the longitudinal axis AL shown by the arrow HH in FIG. 8. The second direction HH is substantially opposite the first direction GG. Because the angle eF2 defined by the axis $A_{F2}$ of the second face 316 of the notch 315 and the longitudinal axis AL is obtuse with respect to the second direction HH, the loop 412 of the suture 410 is released from the notch 315 as the delivery device 310 is moved in the second direction HH. Said another way, when the delivery device 310 is moved in the second direction HH, the second face 316 of the notch 315 exerts a force on the loop 412 of the suture 410 that is normal to the second face 316. This force pushes the loop 412 of the suture 410 out of the notch 315. Once the loop 412 of the suture 410 is released from the notch 315, the medical practitioner can remove the delivery device 310 from the tissue of the patient by continuing to move the delivery device 310 in the second direction HH.

Figure 9:
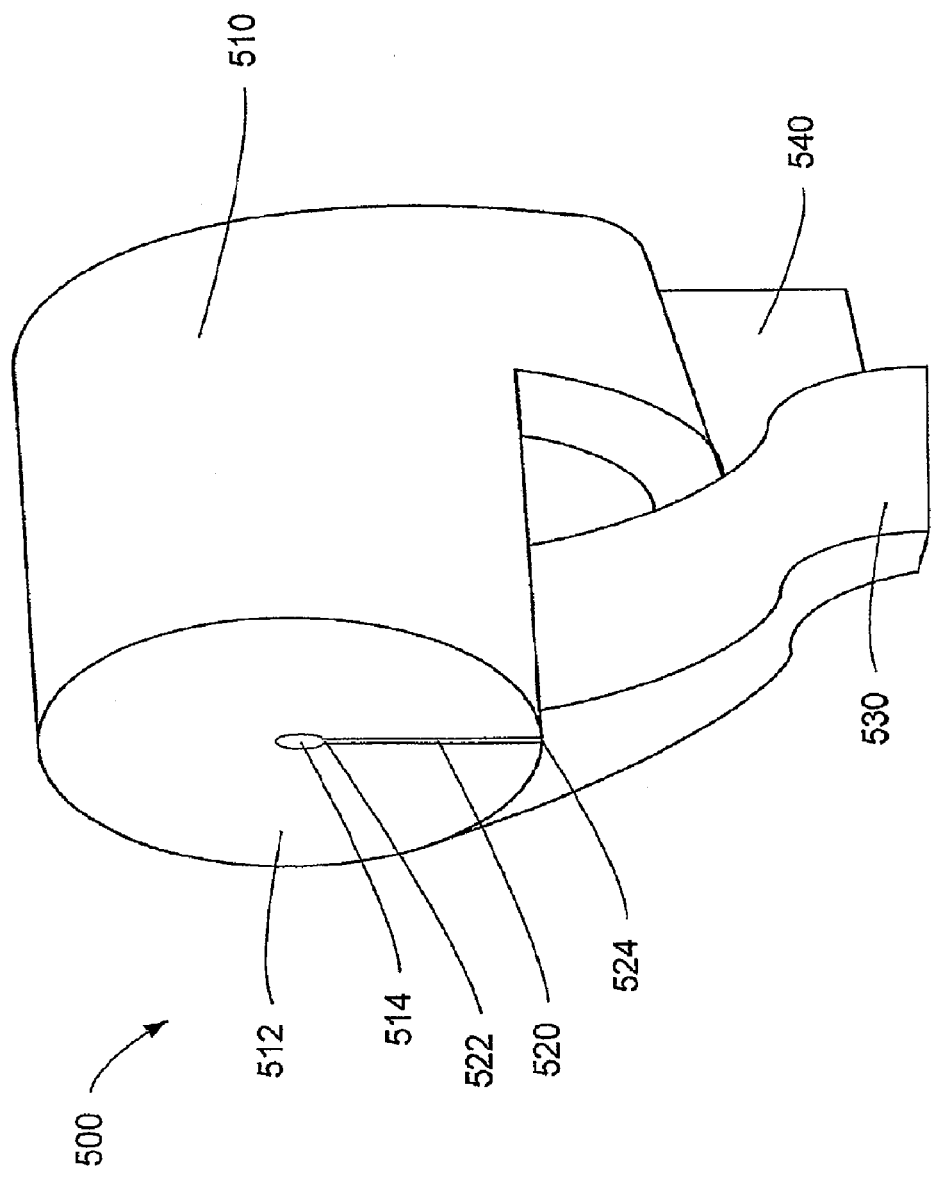
FIG. 9 is a perspective view of an adjustable stop, according to an embodiment.

FIG. 9 is a side perspective view of an adjustable stop 500, according to another embodiment. The adjustable stop 500 is configured to limit the depth the delivery device can be inserted into a tissue of a patient. The adjustable stop 500 includes a body portion 510, a first leg portion 530 and a second leg portion 540. The body portion 510 includes a first face 512 and a second face (not shown). The first face 512 of the body portion 510 are shown in FIG. 9 as being substantially circular in shape. In other embodiments, faces of the body portion can be any other suitable shape, such as, for example, triangular, square, and/or hexagonal.

The body portion 510 defines a lumen 514 and a slit 520. The lumen 514 extends the entire length of the body portion 510 of the adjustable stop 500. Said another way, the lumen extends from the first face 512 of the body portion 510 to the second face (not shown) of the body portion 510.

The first leg portion 530 of the adjustable stop 500 and the second leg portion 540 of the adjustable stop 540 extend from the body portion 510 of the adjustable stop 500. The first leg portion 530 and the second leg 540 portion cross each other as shown in FIG. 9.

Figure 10:
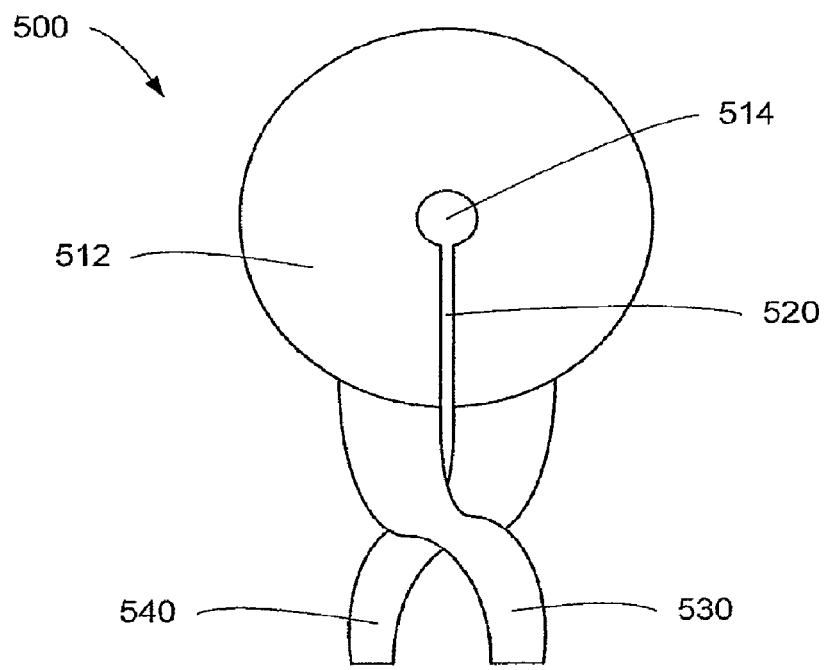
FIGS. 10 and 11 are front views of the adjustable stop of FIG. 9 in a first configuration and a second configuration, respectively.
Figure 11:
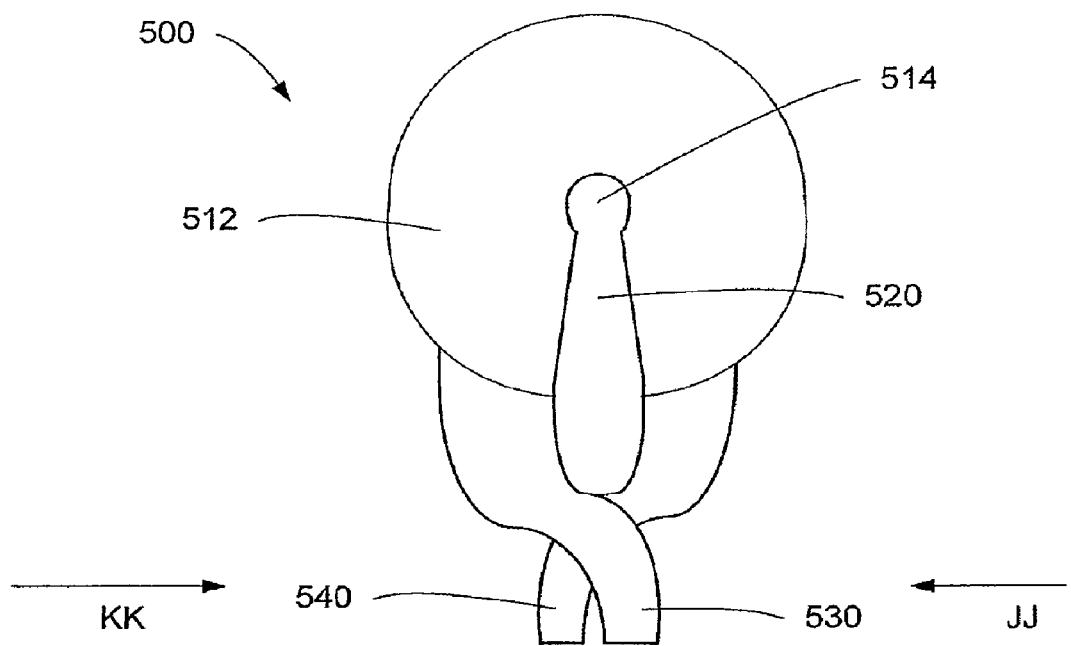

The adjustable stop 500 has a first configuration and a second configuration, as shown in FIG. 10 and FIG. 11 respectively. When the adjustable stop 500 is in its first configuration (FIG. 10), the lumen 514 has a size that is substantially equal to the size of a delivery device, such as the delivery device 310 shown and described in FIG. 5. Additionally, when the adjustable stop 500 is in its first configuration, the slit 520 has a width that is less than a width of the delivery device. As such, a delivery device not disposed within the lumen 514 is prevented from passing through the slit 520 and into the lumen 514 and a delivery device disposed within the lumen 514 (see e.g., FIG. 12) is prevented from passing through the slit 520 to be removed from the lumen 514. Further, the position of the adjustable stop 500 with respect to a delivery device disposed within the lumen 514 is fixed. Thus, the adjustable stop 500 is unable to move with respect to a delivery device disposed within the lumen 514 when the adjustable stop 500 is in its first configuration.

When the adjustable stop 500 is in its second configuration (FIG. 11) the lumen 514 has a size that is greater than the size of the delivery device. As such, the delivery device can be inserted into the lumen 514 and the adjustable stop 500 can move with respect to the delivery device. For example, the adjustable stop 500 can slide along the delivery device in a direction substantially parallel to a longitudinal axis defined by the delivery device.

The width of the slit 520 in the second configuration is greater than the width of the slit 520 in the first configuration. The width of the slit 520 in the second configuration, however, is smaller than the width of the delivery device. As such, similar to the first configuration, the delivery device cannot pass through the slit 520. This prevents the delivery device from inadvertently being removed from the lumen 514 when the adjustable stop 500 is in its second configuration.

The adjustable stop 500 can be moved from its first configuration (FIG. 10) to its second configuration (FIG. 11) by squeezing the first leg portion 530 and the second leg portion 540 together. Specifically, to move the adjustable stop 500 into its second configuration a force in the direction shown by the arrow JJ is exerted on the first leg portion 530 and a force in the direction shown by the arrow KK is exerted on the second leg portion 540. This causes the lumen 514 and the slit 520 to expand. As discussed above, once in the second configuration, the adjustable stop 500 can be coupled to the delivery device and can be moved with respect to the delivery device.

The adjustable stop 500 is biased in its first configuration. Thus, to return the adjustable stop 500 to its first configuration, the force exerted on the first leg portion 530 and the force exerted on the second leg portion 540 are released. This causes the lumen 514 and the slit 520 to contract back to the first configuration.

The adjustable stop 500 is configured to help limit the distance that a distal end portion of the delivery device can be inserted into the tissue of the patient. The distance that the distal end portion of the delivery device can be inserted into the patient is substantially equal to the distance between the distal end portion of the delivery device and the adjustable stop 500. Having an adjustable stop 500 prevents a medical practitioner from inserting the distal end portion of the delivery device into the tissue of the patient further than expected, causing unwanted harm. The adjustable stop 500 also provides the medical practitioner with the ability to determine a depth within the tissue of the patient where a distal end portion of a suture and/or a tissue anchor of the suture is to be disposed, and, using the adjustable stop 500, setting the delivery device to deliver the distal end portion of the suture 500 and/or the tissue anchor of the suture to this depth, as further described in detail herein.

Figure 12:
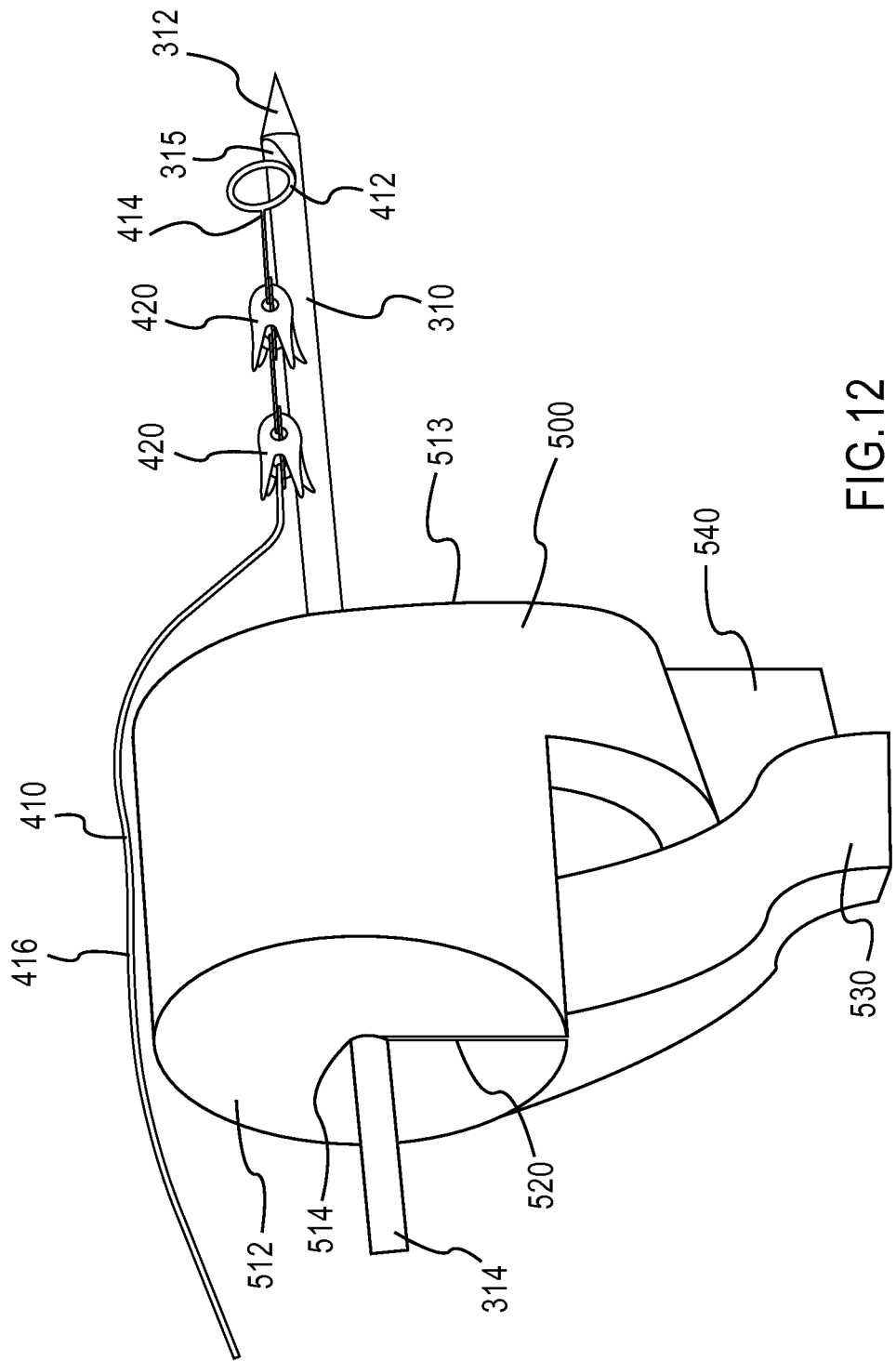
FIG. 12 is a perspective view of the adjustable stop of FIG. 9 and the suture of FIG. 6 coupled to the delivery device of FIG. 5.

In use, the adjustable stop 500 is moved into its second configuration and coupled to the delivery device. FIG. 12 shows the adjustable stop 500 coupled to the delivery device 310 of FIG. 5. The adjustable stop 500 can be moved with respect to the delivery device 310 in order to set a depth to which a distal end portion 414 of a suture 410 or a tissue anchor 420 of the suture 410 will be disposed. Once the adjustable stop 500 is in the desired position with respect to the delivery device 310, it is moved from its second configuration to its first configuration. As described above, when the adjustable stop 500 is in its first configuration, the position of the adjustable stop 500 with respect to the delivery device 310 is substantially fixed.

A suture 410 is releasably coupled to the distal end portion 312 of the delivery device 310. This can be accomplished by any of the methods described above. The distal end portion 312 of the delivery device 310 is inserted into the tissue of the patient in a first direction until the second face (not shown) of the adjustable stop contacts the outer surface of the tissue. Once the second face of the adjustable stop contacts the outer surface of the tissue, the distal end portion 312 of the delivery device 310 cannot be inserted deeper into the tissue (i.e., the skin near the insertion site). The suture is released from the distal end portion of the delivery device and the distal end portion of the delivery device removed from the tissue of the patient by moving the delivery device in a second direction, substantially opposite the first direction.

Figure 13:
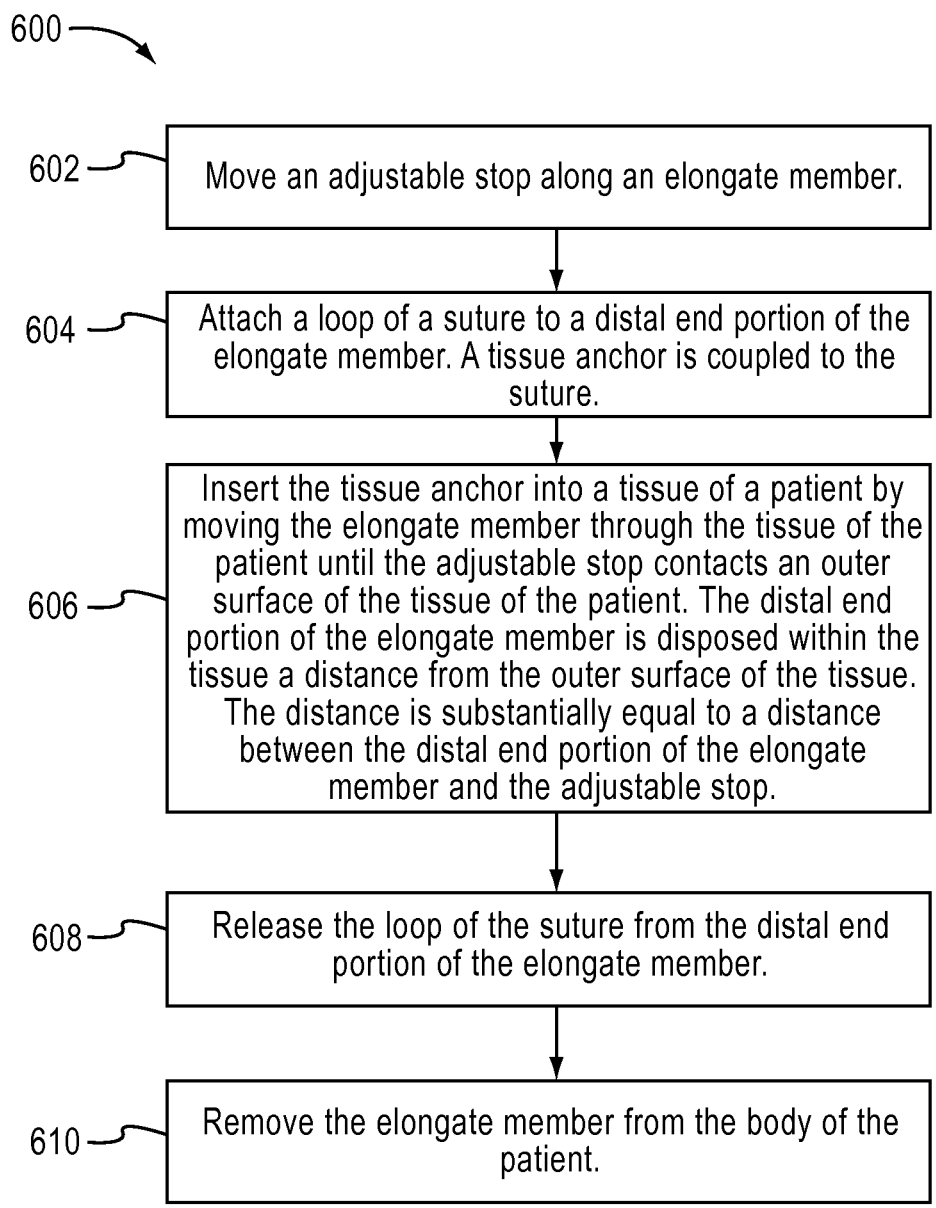
FIG. 13 is a flow chart illustrating a method of placing a suture within a body of a patient according to an embodiment.

FIG. 13 is a flow chart illustrating a method 600 of placing a suture within a body of a patient, according to another embodiment. The method 600 includes moving an adjustable stop along an elongate member, at 602. The elongate member is a portion of a delivery device. In some embodiments, the delivery device is structurally and functionally similar to the delivery devices shown and described herein. In some embodiments, the adjustable stop is structurally and functionally similar to the adjustable stops shown and described herein.

A loop of a suture is attached to a distal end portion of the elongate member, at 604. A tissue anchor is coupled to the suture. The suture can be attached to the distal end portion of the elongate member by any suitable method. In some embodiments, for example, the suture has a loop configured to attach to a notch defined by the elongate member as shown and described herein. In other embodiments, the suture can be attached to the distal end portion of the elongate member using a clip, an adhesive, glue and/or any other attachment mechanism known in the art.

The tissue anchor is inserted into a tissue of a patient by moving the elongate member through the tissue of the patient until the adjustable stop contacts an outer surface of the tissue of the patient, at 606. The distal end portion of the elongate member is disposed within the tissue a distance from the outer surface of the tissue. The distance is substantially equal to a distance between the distal end portion of the elongate member and the adjustable stop.

The loop of the suture is released from the distal end portion of the elongate member. This can be done by any suitable method. In some embodiments, for example, the elongate member is moved in a direction substantially opposite the direction in which the elongate member was moved to insert the tissue anchor, as shown and described herein. In such embodiments, the movement in the opposite direction causes the loop of the suture to release from the distal end portion of the elongate member. In other embodiments, the loop of the suture can be released from the distal end portion of the elongate member by releasing a clip, waiting for an adhesive to dissolve, moving a switch on a handle, and/or the like.

The elongate member is then removed from the body of the patient. This can be done by moving the elongate member in a direction substantially opposite the direction in which the elongate member was moved to insert the tissue anchor.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, while a single type of adjustable stop is described, any adjustable stop capable of limiting the depth a distal end portion of a delivery device can be inserted into a tissue can be used. For example, the adjustable stop might have a different shape, size, and/or method of moving between its first configuration and its second configuration. In some embodiments, for example, the adjustable stop is moved between its first configuration and its second configuration by use of a switch, a dial, a screw, and/or any other mechanism known in the art.

Although various embodiments have been described as having particular features and/or combinations of components, other embodiments are possible having a combination of any features and/or components from any of embodiments where appropriate.

An apparatus includes an elongate member having a distal end portion and a proximal end portion. The elongate member defines a longitudinal axis. The distal end portion of the elongate member defines a notch having a face defining an axis. The axis of the face and the longitudinal axis define an acute angle with respect to a first direction along the longitudinal axis. The notch is configured to retain a loop of a suture when the elongate member is moved through a tissue of a patient in the first direction along the longitudinal axis. The notch is configured to release the loop of the suture when the elongate member is moved through the tissue of the patient in a second direction different than the first direction. The suture has at least one tissue anchor configured to be disposed within the tissue of the patient.

In some embodiments, the loop of the suture remains within the tissue of the patient when the elongate member is moved in the second direction.

In some embodiments, the apparatus further includes an adjustable stop coupled to the elongate member. The adjustable has a first configuration and a second configuration. The adjustable stop is configured to move with respect to the elongate member when in the first configuration and is configured to maintain its position with respect to the elongate member when in the second configuration. The adjustable stop is configured to limit the distance between an outer surface of the tissue and the distal end portion of the elongate member when the adjustable stop is in its second configuration and the elongate member is inserted into the tissue of the patient such that the adjustable stop contacts the outer surface of the tissue.

In some embodiments, the tissue anchor is configured to allow movement of the suture through the tissue of the patient in the first direction and configured to limit movement of the suture through the tissue of the patient in the second direction. In some embodiments, the distal end portion of the elongate member includes a tissue piercing portion configured to penetrate the tissue of the patient.

In some embodiments, the elongate member is substantially solid. In some embodiments, the elongate member is substantially rigid. In some embodiments, the face of the notch is a first face of the notch and the notch has a second face defining an axis. The axis of the second face and the longitudinal axis define an obtuse angle with respect to the second direction.

In some embodiments, a method includes sliding an adjustable stop along an elongate member. A loop of a suture is attached to a distal end portion of the elongate member. A tissue anchor is coupled to the suture. The tissue anchor is inserted into a tissue of a patient by moving the elongate member through the tissue of the patient until the adjustable stop contacts an outer surface of the tissue of the patient. The distal end portion of the elongate member is disposed within the tissue a distance from the outer surface of the tissue. The distance is substantially equal to a distance between the distal end portion of the elongate member and the adjustable stop. The loop of the suture is released from the distal end portion of the elongate member and the elongate member is removed from the body of the patient.

In some embodiments, the inserting includes penetrating the tissue of the patient with the distal end portion of the elongate member. In some embodiments, the inserting includes moving the elongate member through the tissue of the patient in a first direction and the releasing includes moving the elongate member in a second direction substantially opposite the first direction.

In some embodiments, the releasing the loop of the suture from the distal end portion of the elongate member includes moving the elongate member with respect to the tissue of the patient. In some embodiments, the attaching includes inserting the loop of the distal end portion of the suture into a notch defined by the distal end portion of the elongate member.

In some embodiments, the apparatus includes an elongate member having a distal end portion and a proximal end portion and an adjustable stop movably coupled to the elongate member. The distal end portion of the elongate member defines a notch configured to releasably retain a loop of a suture when the elongate member is inserted into a tissue of a patient a distance. The adjustable stop is configured to allow a user to determine the distance the elongate member is inserted into the tissue.

In some embodiments, the adjustable stop defines a face configured to contact an outer portion of the tissue when the elongate member is inserted into the tissue the distance. In some embodiments, the distance is a first distance and the adjustable stop has a first position with respect to the elongate member and a second position with respect to the elongate member. The elongate member is configured to be inserted into the tissue of the patient the first distance when the adjustable stop is in the first position. The elongate member is configured to be inserted into the tissue of the patient a second distance when the adjustable stop is in the second position. The second distance is greater than the first distance.

In some embodiments, the elongate member defines a longitudinal axis and is configured to be inserted into the tissue of the patient in a direction substantially along the longitudinal axis. In some embodiments, the adjustable stop is configured to move with respect to the elongate member. In some embodiments, the notch is configured to retain the loop of the suture when the elongate member is moved in a first direction through the tissue of the patient. The notch is configured to release the loop of the suture when the elongate member is moved in a second direction substantially opposite the first direction.

In some embodiments, the elongate member is substantially solid. In some embodiments, the elongate member is substantially rigid. In some embodiments, at least one tissue anchor configured to be disposed within the tissue of the patient is coupled to the suture.

In some embodiments, an apparatus includes an elongate member having a distal end portion and a proximal end portion. The elongate member defines a longitudinal axis and an outer perimeter. The distal end portion of the elongate member has a tissue piercing tip and an oblique shoulder facing toward the tissue piercing tip. The oblique shoulder is disposed proximal to the tissue piercing tip along the longitudinal axis and is within the outer perimeter defined by the elongate member.

In some embodiments, the oblique shoulder is configured to retain a loop of a suture when the elongate member is moved through a tissue of a patient in the first direction along the longitudinal axis. The oblique shoulder is configured to release the loop of the suture when the elongate member is moved through the tissue of the patient in a second direction different than the first direction. The suture has at least one tissue anchor configured to be disposed within the tissue of the patient.

In some embodiments, the elongate member is substantially solid. In some embodiments, the elongate member is substantially rigid. In some embodiments the apparatus further includes an adjustable stop coupled to the elongate member. The adjustable stop has a first configuration and a second configuration. The adjustable stop is configured to move with respect to the elongate member when in the first configuration and is configured to maintain its position with respect to the elongate member when in the second configuration. The adjustable stop is configured to limit the distance between an outer surface of the tissue and the distal end portion of the elongate member when the adjustable stop is in its second configuration and the elongate member is inserted into the tissue of the patient such that the adjustable stop contacts the outer surface of the tissue.

In some embodiments, a medical device includes an elongate member having a distal end portion and a proximal end portion, a suture having a distal end portion and a proximal end portion and an anchor coupled to the suture. The distal end portion of the elongate member defines a notch. The distal end portion of the suture has a loop configured to be inserted into the notch. The notch is configured to retain the loop of the suture when the elongate member is inserted into a tissue of a patient. The anchor is configured to retain the suture within the tissue of the patient when the suture is disposed within the tissue of the patient and the elongate member is removed from the tissue of the patient.

In some embodiments, the anchor is configured to allow movement of the suture through the tissue of the patient in a first direction and is configured to help prevent movement of the suture through the tissue of the patient in a second direction substantially opposite the first direction.

In some embodiments, the medical device further includes an adjustable stop coupled to the elongate member. The adjustable stop has a first configuration and a second configuration. The adjustable stop is configured to move with respect to the elongate member when in the first configuration. The adjustable stop is configured to maintain its position with respect to the elongate member when in the second configuration. The adjustable stop configured to limit the distance between an outer surface of the tissue and the distal end portion of the elongate member when the adjustable stop is in its second configuration and the elongate member is inserted into the tissue of the patient such that the adjustable stop contacts the outer surface of the tissue.

In some embodiments, the notch of the distal end portion of the elongate member has a face defining an axis. The axis and a longitudinal axis defined by the elongate member define an acute angle with respect to a distal direction.

In some embodiments, the distal end portion of the elongate member includes a tissue piercing portion configured to penetrate the tissue of the patient. In some embodiments, the elongate member is substantially solid. In some embodiments, the elongate member is substantially rigid.

What is claimed is:
1. An apparatus, comprising:
a suture having an attachment portion;
at least one tissue anchor being coupled to the suture; and
an elongate member having a distal end portion and a proximal end portion, the elongate member defining a longitudinal axis, the distal end portion of the elongate member defining a notch, the notch having a face defining an axis, the axis of the face and the longitudinal axis defining an acute angle with respect to a first direction along the longitudinal axis, the notch configured to retain the attachment portion of the suture when the elongate member is moved through a tissue of a patient in the first direction along the longitudinal axis, the notch configured to release the attachment portion of the suture when the elongate member is moved through the tissue of the patient in a second direction different than the first direction,
the at least one tissue anchor having a first coupling portion and a second coupling portion, the first coupling portion and the second coupling portion configured to couple the suture, a first portion of the suture extending distally beyond a distal end of the at least one tissue anchor, a second portion of the suture extending proximally beyond a proximal end of the at least one tissue anchor,
the at least one tissue anchor including a body portion disposed between the first coupling portion and the second coupling portion, the at least one tissue anchor including a first set of retaining members that extend from a first side of the body portion and a second set of retaining members that extend from a second side of the body portion, the second side being opposite to the first side, the second coupling portion being disposed between the first set of retaining members and the second set of retaining members.

2. The apparatus of claim 1, wherein the attachment portion includes a loop, and the loop is configured to remain within the tissue of the patient when the elongate member is moved in the second direction.

3. The apparatus of claim 1, further comprising:
an adjustable stop coupled to the elongate member, the adjustable stop having a first configuration and a second configuration, the adjustable stop configured to move with respect to the elongate member when in the first configuration, the adjustable stop configured to maintain its position with respect to the elongate member when in the second configuration, the adjustable stop configured to limit the distance between an outer surface of the tissue and the distal end portion of the elongate member when the adjustable stop is in its second configuration and the elongate member is inserted into the tissue of the patient such that the adjustable stop contacts the outer surface of the tissue.

4. The apparatus of claim 1, wherein the at least one tissue anchor is configured to allow movement of the suture through the tissue of the patient in the first direction, the at least one tissue anchor being configured to limit movement of the suture through the tissue of the patient in the second direction.

5. The apparatus of claim 1, wherein the distal end portion of the elongate member includes a tissue piercing portion configured to penetrate the tissue of the patient.

6. The apparatus of claim 1, wherein the elongate member is substantially solid.

7. The apparatus of claim 1, wherein the elongate member is substantially rigid.

8. The apparatus of claim 1, wherein the face of the notch is a first face of the notch, the notch having a second face defining an axis, the axis of the second face and the longitudinal axis defining an obtuse angle with respect to the second direction.

9. The apparatus of claim 1, wherein the first coupling portion and the second coupling portion define a first opening and a second opening, respectively, the suture extending through the first opening and being coupled to the first coupling portion such that a first loop is formed by the suture around the first coupling portion, the suture extending from the first loop through the second opening and being coupled to the second coupling portion such that a second loop is formed by the suture around the second coupling portion.

10. An apparatus, comprising:
a suture having an attachment portion;
at least one tissue anchor being coupled to the suture;
an elongate member having a distal end portion and a proximal end portion, the distal end portion of the elongate member defining a notch configured to releasably retain the attachment portion of the suture when the elongate member is inserted into a tissue of a patient a distance,
the at least one tissue anchor having a first coupling portion and a second coupling portion, the first coupling portion and the second coupling portion configured to couple the suture, a first portion of the suture extending distally beyond a distal end of the at least one tissue anchor, a second portion of the suture extending proximally beyond a proximal end of the at least one tissue anchor,
the at least one tissue anchor including a body portion disposed between the first coupling portion and the second coupling portion, the at least one tissue anchor including a first set of retaining members that extend from a first side of the body portion and a second set of retaining members that extend from a second side of the body portion, the second side being opposite to the first side, the second coupling portion being disposed between the first set of retaining members and the second set of retaining members; and
an adjustable stop having a body portion being movably coupled to the elongate member, the adjustable stop configured to allow a user to determine the distance the elongate member is inserted into the tissue, the adjustable stop defining a lumen and a slit, the slit extends along a plane, the plane is disposed substantially parallel to the lumen and extends towards an outer perimeter of the body portion of the adjustable stop, the adjustable stop having a first leg member and a second leg member, the first leg member having a first end portion coupled to the body portion of the adjustable stop and a second end portion, the plane being disposed between the first end portion of the first leg member and the second end portion of the first leg member, the second leg member having a first end portion coupled to the body portion of the adjustable stop and a second end portion, the plane being disposed between the first end portion of the second leg member and the second end portion of the second leg member.

11. The apparatus of claim 10, wherein the adjustable stop defines a face, the face configured to contact an outer portion of the tissue when the elongate member is inserted into the tissue the distance.

12. The apparatus of claim 10, wherein the distance is a first distance, the adjustable stop having a first position with respect to the elongate member and a second position with respect to the elongate member, the elongate member configured to be inserted into the tissue of the patient the first distance when the adjustable stop is in the first position, the elongate member configured to be inserted into the tissue of the patient a second distance when the adjustable stop is in the second position, the second distance being greater than the first distance.

13. The apparatus of claim 10, wherein the elongate member defines a longitudinal axis, the elongate member being configured to be inserted into the tissue of the patient in a direction substantially along the longitudinal axis.

14. The apparatus of claim 10, wherein the adjustable stop is configured to move with respect to the elongate member.

15. The apparatus of claim 10, wherein the notch is configured to retain the attachment portion of the suture when the elongate member is moved in a first direction through the tissue of the patient, the notch being configured to release the attachment portion of the suture when the elongate member is moved in a second direction substantially opposite the first direction.

16. The apparatus of claim 10, wherein the elongate member is substantially solid.

17. The apparatus of claim 10, wherein the first coupling portion and the second coupling portion define a first opening and a second opening, respectively, the suture extending through the first opening and being coupled to the first coupling portion such that a first loop is formed by the suture around the first coupling portion, the suture extending from the first loop through the second opening and being coupled to the second coupling portion such that a second loop is formed by the suture around the second coupling portion.

18. An apparatus, comprising:
a suture having an attachment portion;
a tissue anchor being coupled to the suture; and
an elongate member having a distal end portion and a proximal end portion, the elongate member defining a longitudinal axis, the distal end portion of the elongate member defining a notch, the notch being configured to retain the attachment portion of the suture when the elongate member is moved through a tissue of a patient in a first direction along the longitudinal axis, the notch configured to release the attachment portion of the suture when the elongate member is moved through the tissue of the patient in a second direction different than the first direction,
the tissue anchor having a first coupling portion and a second coupling portion, the first coupling portion and the second coupling portion defining a first opening and a second opening, respectively, the suture extending through the first opening and being coupled to the first coupling portion such that a first loop is formed by the suture around the first coupling portion, the suture extending from the first loop through the second opening and being coupled to the second coupling portion such that a second loop is formed by the suture around the second coupling portion,
the tissue anchor including a body portion disposed between the first coupling portion and the second coupling portion, the tissue anchor including a first set of retaining members that extend from a first side of the body portion and a second set of retaining members that extend from a second side of the body portion, the second side being opposite to the first side, the second coupling portion being disposed between the first set of retaining members and the second set of retaining members.

19. The apparatus of claim 18, wherein the attachment portion of the suture includes a loop portion.

* * * * *